United States Patent

Kroneis et al.

[11] Patent Number: 4,703,182
[45] Date of Patent: Oct. 27, 1987

[54] ARRANGEMENT FOR FLUORESCENCE-OPTICAL MEASUREMENT OF CONCENTRATIONS OF SUBSTANCES CONTAINED IN A SAMPLE

[75] Inventors: Herbert Kroneis; Helmut Offenbacher, both of Graz, Austria

[73] Assignee: AVL Gesellschaft für Verbrennungskraftmaschinen und Messtechnik m.b.H. Prof.Dr.Dr.h.c. Hans List, Graz, Austria

[21] Appl. No.: 776,586

[22] Filed: Sep. 16, 1985

[30] Foreign Application Priority Data

Sep. 17, 1984 [AT] Austria ................. 2955/84

[51] Int. Cl.$^4$ ............................. G01N 21/64
[52] U.S. Cl. ................. 250/458.1; 250/365; 250/461.1; 250/461.2; 436/527
[58] Field of Search ........... 250/461.2, 461.1, 458.1, 250/483.1, 365, 227; 356/445; 436/172, 164, 527, 531, 805, 807; 422/57

[56] References Cited

U.S. PATENT DOCUMENTS

| | | | |
|---|---|---|---|
| 3,604,927 | 9/1971 | Hirschfeld | 250/483.1 |
| 3,612,866 | 10/1971 | Stevens | 250/483.1 |
| 3,669,545 | 6/1972 | Gilby | 356/320 |
| 4,050,895 | 9/1977 | Hardy et al. | 436/527 |
| 4,447,546 | 5/1984 | Hirschfeld | 436/527 |
| 4,532,425 | 7/1985 | Abileah et al. | 250/363 S |
| 4,564,598 | 1/1986 | Briggs | 436/501 |
| 4,587,101 | 5/1986 | Marsoner et al. | 422/56 |

FOREIGN PATENT DOCUMENTS

| | | |
|---|---|---|
| 109959 | 5/1984 | European Pat. Off. . |
| 109958 | 5/1984 | European Pat. Off. . |
| 2508637 | 9/1976 | Fed. Rep. of Germany . |
| 1190583 | 5/1970 | United Kingdom . |

Primary Examiner—Janice A. Howell
Assistant Examiner—Constantine Hannaher
Attorney, Agent, or Firm—Watson, Cole, Grindle & Watson

[57] ABSTRACT

An arrangement for the fluorescence-optical measurement of concentrations of substances contained in a sample includes a detector, a light source and a sensor element that includes a carrier element, the carrier element having an indicator layer on a portion thereof and an indicator-free surface, the carrier element being transparent to the radiation used, and having a refractive index which is greater than that of the ambient medium at the indicator-free surface, the light space being positioned such that the transmission of light from the light source to the indicator layer, and from there to the detector, is achieved, at least partially, by total reflection in the carrier element.

13 Claims, 10 Drawing Figures

ARRANGEMENT FOR FLUORESCENCE-OPTICAL MEASUREMENT OF CONCENTRATIONS OF SUBSTANCES CONTAINED IN A SAMPLE

BACKGROUND OF THE INVENTION

This invention relates to an arrangement for the fluorescence-optical measurement of the concentration of substances contained in a sample, comprising a light source for excitation radiation, a sensor element fluorescing upon excitation in accordance with the substance concentration to be determined, and a detector for emission radiation, the sensor element comprising a carrier element which can be brought into contact, at least indirectly, with the sample to be measured via at least part of its surface, and which is transparent for excitation and emission radiation and has a refractive index $n_1$ that is higher than the refractive index $n_3$ of the ambient medium so that light rays, whose angles of incidence $\alpha_1$—measured from the normal on the boundary surface between carrier element and ambient medium—are bigger than $\alpha_{G1,3} = \arcsin n_3/n_1$, are propagated in the carrier element by total reflection.

DESCRIPTION OF THE PRIOR ART

An arrangement of the above type is shown in U.S. Pat. No. 3,604,927. In this known type of arrangement the sample is excited by evanescent waves which arise in the medium of lower optical density under conditions of total reflection at the boundary surface between the medium with higher and that with lower optical density, and which quickly decay exponentially. The sample must therefore have a refractive index smaller than that of the totally reflecting carrier element. Because of the specific angles required for the directed, collimated excitation beam the surfaces for the entrance and exit of excitation light from the carrier element must be given a special treatment. This necessitates a complex measuring system with high demands on exact positioning, the low penetration of the evanescent waves into the fluorescent sample medium yielding low signal intensities only. Besides it should be noted that the optical characteristics of the sample in the area of the evanescent waves, e.g., light absorption by non-fluorescent substances, will influence the measuring signals.

Arrangements for measuring physical or chemical parameters, above all the concentrations of substances of interest, by means of luminescent indicators, are described. in DE OS No. 25 08 637, U.S. Pat. No. 3,612,866, GB-PS No. 1 190 583, EP-O No. 109 959-A1, and EP-O No. 109 958-A1, for instance.

Such arrangements are based on sensor elements provided with luminescent layers which are brought into contact with the sample and—upon excitation by light—will emit light whose spectrum and/or intensity will depend on the quantity to be measured. Part of the light emitted by the sensor element is measured by detectors, which will permit determination of the magnitude of the sample parameters of interest in accordance with the physical or chemical laws of the interaction of sample medium and luminescent layer or indicator substance.

The disadvantage of the above arrangements is that the yield of emission light that may be attributed to the quantity to be determined, is relatively small, which will limit the resolution according to the given sensitivity of the detectors (photodetectors) used. This situation cannot be counterbalanced even by an increase in the intensity of the excitation light since the luminescent indicators known and used in this context are subject to varying degrees of photodecomposition whose reaction rate is proportional to the amount of light absorbed. Thus an increase of the intensity of excitation light would directly entail aging of the indicator and would thus affect measuring accuracy.

SUMMARY OF THE INVENTION

It is an object of the present invention to improve an arrangement of the afore-mentioned type in such a way as to eliminate the above disadvantages and, above all, to increase the yield of emission light arriving at the detector for a given indicator substance, without having to put up with the disadvantages that are usually encountered when the intensity of the excitation light is increased.

According to the invention this is achieved by covering at least part of the surface of the carrier element with a layer of an indicator substance of a given refractive index $n_2$, whose side facing away from the carrier element is in contact with the sample during the process of measurement, and providing that in the area of the carrier element, that is in contact with the sample during measurement via the indicator layer, the emission radiation reaching the detector, and/or the excitation radiation, should have angles $\alpha_1$ which are smaller than $\alpha_{G1,2} = \arcsin n_2/n_1$. The carrier element coated with the indicator thus has surfaces which are at least partially reflecting and whose shape and position are matched with the system of excitation and/or detection in such a way that the carrier element will collimate and transmit excitation and/or emission light, i.e., directed towards the indicator layer and/or the detector.

The term carrier element in this context usually denotes a transparent body, part of whose surface at least is in contact with the luminescent indicator layer, the carrier element acting as a boundary for the indicator layer in this area, and the position of the indicator layer relative to the carrier element being fixed. The indicator layer which will fluoresce upon excitation, may be bonded to the carrier element by chemical or physical interactions with the latter. Methods of bonding include adhesion of liquid films, adhesion or chemical bonding (covalent bonding) of polymer coats - incorporating luminescent pigments, adsorption or chemical bonding of luminescent pigments directly to the carrier element.

Reflection in the carrier element may be achieved either by mirror-coating the respective surfaces according to known methods, or by observing the conditions for total reflection. Total reflection occurs if light from a medium of higher optical density falls in upon the boundary surface with a medium of lower optical density, and if the angle of incidence is greater than the limiting angle for total reflection.

In general, the limiting angle is defined by the difference in refractive indices of the two adjacent media according to equation 1.

EQUATION 1

$$\sin \alpha_{Ga,b} = n_b/n_a;$$

/$\alpha_{Ga,b}$: limiting angle for total reflection
$n_a$: refractive index of the medium of higher optical density $n_b$: refractive index of the medium of lower optical density The latter case of total reflection at the boundary surfaces of media of different optical densities is preferred vis-à-vis the other possibility, i.e., of reflection at mirror-coated surfaces. Among the advantages of total reflection at boundary surfaces are lower manufacturing costs for sensor elements with totally reflecting surfaces, and, above all, the possibility of separating the paths of excitation and emission light, and thus discriminating between the two (emission light=luminescent light). In the following, this possibility of discrimination will be pointed out separately for each of the preferred variants of the invention; it is based on the angle dependence of total reflection (light rays with angles of incidence $> \alpha_{Ga,b}$ are reflected totally, and thus remain in the medium of the carrier element, whereas light rays with angles of incidence $< \alpha_{Ga,b}$ are refracted away from the normal, and thus leave the carrier element).

As mentioned before, care should be taken that the environment of the surfaces to be used for total reflection should consist of media whose refractive indices are lower than that of the carrier medium.

Examples of carrier and ambient materials are:

| Material | Refractive Index |
| --- | --- |
| Carrier element | |
| glass | 1.46–1.9 (according to type of glass used) |
| quartz glass | 1.46 |
| Plexiglas ® (synthetic resin material) | 1.50 |
| polycarbonates | 1.60 |
| unsaturated polyesters | 1.52 |
| Ambient medium | |
| air | 1.00 |
| water | 1.33 |
| silicones | 1.40–1.58 |
| PVC plasticized | 1.5 |

Regarding the ambient medium, polymer (silicones, PVC) may be employed for coating or embedding of the carrier elements, at the same time serving as supports or links to such supports.

A preferred variant of the invention is concerned with the frequently used technique of measuring luminescence by reflectance ("remission"), for instance with the use of two-armed bundle of optical fibers as a coupling element between light source, sensor and photodetector. In this variant the carrier element has the shape of a cylinder or prism, and one of its top/bottom surfaces which is facing away from the indicator layer, is in contact with one end of a light-transmitting coupling element, preferably a multi-armed bundle of optical fibers utilizing total reflection, whose other end is connected to the light source and the detector, and the side surface(s) of the carrier element is/are approximately normal to the above top/bottom surface.

The common end of the bundle of optical fibers which are randomly mixed in the area of the carrier element, may be used to carry excitation light from the light source to the indicator layer, as well as liminescent light from the indicator layer to the detector.

The cylindrical carrier element for the fluorescent indicator layer has a "totally reflecting" side surface, for instance. The top surface of the cylindrical carrier element which is cut normally to the cylinder axis, borders on a two-armed bundle of optical fibers; for optimum results the diameter of the carrier element equals the diameter of the adjacent end of the bundle of optical fibers. The bottom surface of the carrier element is coated with the indicator layer at least partially, and may vary in shape.

In the simplest case this surface also is cut normally to the cylinder axis, or the axis of the prism if the carrier element is configured as a prism. A particular advantage of such carrier elements is that the light paths for the excitation radiation also are bounded by the reflecting side surface such that the excitation light is collimated onto the indicator layer, and interactions between the light and the sensor environment are avoided.

In order to prevent (partial) reflection of the excitation light back into the coupling element the "bottom surface" of the carrier element carrying the luminescent layer may simply be configured as a plane forming an angle with the top surface, or as a conical recess, or as a convex cone.

In a further development of the invention the bottom surface of the carrier element, which is convered with the indicator layer and faces away from the coupling element, is inclined at an angle $\beta$ relative to the top surface, for which $$\sin\beta > \frac{\sin\alpha_3}{n_1}$$

$\alpha_3$ denoting half of the maximum angle under which the excitation light leaves the coupling element and enters the ambient medium.

The angle $\beta$ substended by this plane or by the generators of the cone and the top surface normal to the axis of the cylinder or prism thus is in accordance with the angle of emergence of light from the optical fibers.

Under the conditions given in equation 2 partially reflected rays of excitation light cannot be propagated in the optical coupling element or in the optical fibers.

EQUATION 2

$$\sin\beta < \frac{\sin\alpha_3}{n_1};$$

$n_1$ = refractive index of the material of the carrier element

This applies under the assumption of the same ambient medium (air, for instance) at the top/bottom surface and the side surface(s) of the carrier element.

The reflected rays of the excitation light will thus leave the top surface of the carrier element only at angles greater than the maximum angle at which light may enter the coupling element from the ambient medium, which implies that they cannot be propagated in the coupling element to the detector.

In an arrangement in which the carrier element is configured as a plate with parallel top and bottom surfaces and the indicator layer is applied on one of these surfaces, total reflection at the parallel surfaces may be utilized for the propagation of excitation light to the indicator, and/or of emission light from the indicator to the detector. The totally reflected rays in the carrier element may enter or leave the plate via lateral faces which are essentially normal to the totally reflecting parallel top and bottom surfaces.

As mentioned before, the dependence of total reflection on specific angles may be utilized here for separating the radiation paths of excitation and emission light.

In this way conventional devices for discriminating between excitation light and luminescent light (monochromators, optical filter may be replaced, at least partly, by a suitable geometry of the carrier element. Thus photodetectors, at a certain distance from the light source, may be positioned in the immediate vicinity of the area where the emission light leaves the carrier element. As no monochromators or filters are needed, and as the detectors may be moved up more closely to the point of origin of the emission light, and as the propagation of light by total reflection is practically without any losses, light yield and measuring accuracy may be increased without having to raise the intensity of the excitation light.

In this context a particularly favorable variant of the invention provides that the light source used for excitation be placed in a position essentially normal to the indicator layer, and that the detector be located at least at one lateral face of the carrier element that is essentially normal to the indicator layer. In this way emission light which is totally reflected inside the carrier element, is detected at least at one lateral face of the carrier element, light excitation occurring without total reflection in the carrier element. The light source is positioned such that the axis of the path of excitation radiation is essentially normal to the indicator layer and thus to the plane parallel carrier plate. Since for the excitation light entering the carrier element the angle conditions for total reflection in the carrier element are not satisfied, no excitation light inside the carrier element will reach the detector(s) via total reflection.

In this context it will be of advantage for the arrangement according to the invention if one top/bottom surface of the carrier element is completely covered by the indicator layer, and if the refractive index $n_2$ of the indicator layer is greater than the refractive index $n_3$ of the ambient medium.

In a preferred development of the invention an aperture is provided between light source and carrier element, which will limit the angle of incidence of the excitation light. This will help to reduce partial reflections of the excitation light in the plane-parallel carrier element. Other collimating devices (e.g., optical lenses) could be provided in order to reduce angular deviations of the excitation light from the optical axis of the excitation radiation. The luminescent indicator layer may cover the entire surface of one of the two parallel top/bottom surfaces, or part of the surface only, for instance only the area which is in contact with the sample.

A particularly favorable variant provides that the aperture between light source and carrier element should only pass excitation light with angles <90° relative to the light path between indicator layer and detector, as this will further reduce the danger that part of the excitation light might still reach the detector(s) on account of partial reflection inside the parallel top/bottom surfaces of the carrier element.

According to yet another development of the invention a coupling layer is provided between the lateral boundary face at the side of the detector and the detector itself, which coupling layer has a refractive index $n_4$ greater than the refractive index $n_3$ of the ambient medium of the carrier element. A refractive index $n_4$ of the coupling layer greater than, or equal to, the refractive index $n_1$ of the carrier element itself, will be preferable, the coupling layer consisting of a polymer material, preferably applied to the detector, according to a favorable variant. In this way the transmission of light from the respective lateral face to the detector may be improved by index-matched media between lateral face and detector (e.g., immersion oil, polymer coating).

The main advantage of these configurations is that a much larger percentage of emission light is radiated off the lateral boundary faces of the carrier element than off the two parallel top/bottom surfaces, one of which carries the indicator layer. Table 1 compares the percentages of emission light radiated off the parallel top/bottom surfaces and the lateral faces of the carrier element. The refractive indices of the media involved in total reflection (carrier element, ambient medium, luminescent indicator layer) are given for three combinations that are often used.

TABLE 1

A comparison of the percentages of emission light radiated off the parallel top/bottom surfaces of a carrier element, and the lateral surfaces normal to these parallel surfaces, the refractive index of the indicator layer varying and the geometry being assumed constant.

| Refractive indices | | | Emission light percentages % of total luminescent light | | Ratio of light percentages |
|---|---|---|---|---|---|
| $n_1$ carriers element | $n_2$ indicator layer | $n_3$ ambient medium | emergence at lateral surfaces | emergence at parallel top/bottom surfaces | lateral/ top-bottom |
| 1.47 (Duran glass) | 1.47 (silicone) | 1.00 (air) | 68.0% | 26.7% | 2.55 |
| 1.47 | 1.40 (silicone) | 1.00 | 68.1% | 29.3% | 2.33 |
| 1.47 | 1.50 (PVC plasticized) | 1.00 | 49.7% | 25.5% | 1.95 |

Table 1 shows that differences in the refractive indices of carrier element and indicator layer are permissible within certain limits. For instance, the light yield at the lateral boundary surface is not affected critically if $n_2 < n_1$. If $n_2 > n_1$, losses in the light yield at the lateral surface will occur due to total reflection between indicator layer and carrier element. This percentage of light which is totally reflected along the indicator layer and which is not shown in Table 1, will nevertheless reach the detector, at least partly, if the indicator layer covers the entire top/bottom surface and is contiguous with the photosensitive layer of the detector at the lateral boundary face of the carrier element.

Table 1 also shows that for realistic combinations of carrier element, indicator layer and ambient medium the percentage of emitted luminescent light radiated off the lateral faces, is 2 to 2½ times as high as the percentage radiated off two parallel top/bottom surfaces.

Another advantage is that the detector(s), as mentioned above, can be positioned directly at the lateral surface(s), whereas for measuring the light radiated off the parallel top/bottom surface, devices, such as filters, for discriminating between excitation light and luminescent light would have to be added between radiating surface and detector.

The detector may be placed at a position essentially normal to the indicator layer, with the light source used for excitation being positioned at a boundary surface of the carrier element that is also essentially normal to the indicator layer. This boundary surface is at a distance from the indicator layer illuminated by the excitation light, which will permit at least one total reflection of the excitation light in the carrier element. Separating the boundary surface from the indicator layer, the carrier element may be provided with a light-proof screen, preferably at a distance from the boundary surface. Thus the excitation light is basically propagated by total reflection with in the plane-parallel carrier element, and the emission light (luminescent light) is detected at least at one of the parallel top/bottom surfaces of the carrier element. In order to avoid partial absorption of the excitation light by the indicator layer, it will be better to apply the luminescent indicator layer only on that part of the parallel top/bottom surfaces which is actually brought into contact with the sample. With this type of arrangement the refractive indices of both carrier element and luminescent indicator layer must be greater than the refractive index of the ambient medium.

The excitation light is reflected totally inside the carrier element and its parallel top/bottom surfaces until a refractive index of the adjoining indicator layer higher than that of the ambient medium, will permit the passage of light through the boundary surface, thereby ensuring that the luminescent molecules are being excited.

Since most of the excitation light (with the exception of straylight) cannot leave the luminescent indicator layer nor the surface on the other side of the carrier plate in the direction of the ambient medium, as it is totally reflected at these surfaces, photodetectors may be positioned either on the surface of the plate opposite of the indicator layer or bordering on a sample chamber (for instance, for measuring transparent gases) or in both places, basically covering the same area as the luminescent indicator layer.

The advantage of this kind of arrangement again is that the detector(s) may be located in closer vicinity of the radiating parallel top/bottom surfaces, since optical filters either are omitted altogether or they are very thin as they are needed for the absorption of scattered excitation light only. In addition, the luminescent light radiated off the parallel top/bottom surfaces may be detected from both sides of the plate, as no light path need be reserved for the excitation radiation in this area.

Preferably, the refractive index of the luminescent indicator layer should be chosen small, without affecting the principal conditation of $n_2 > n_3$. In this way the percentages of luminescent light radiated off the parallel top/bottom surfaces may be increased (cf. Table 1). For the purpose of efficient illumination the refractive index of the carrier element should not significantly exceed that of the luminescent indicator layer, on the other hand, since for $n_1 > n_2$ part of the excitation light at the boundary surface between carrier element and indicator layer is also totally reflected.

In another development of the invention the boundary surface for entrance of the excitation light, the boundary surface for detection of the emission light and the indicator layer are placed at positions normal to one another. Basically, this is a combination of the two preferred variants of the invention described above.

By properly configuring the bottom surface of the plane-parallel carrier element it will therefore be possible to perform both excitation and detection at the lateral surfaces of the carrier element. In addition to detection at the lateral surfaces it will furthermore be possible to detect luminescent light which is radiated off the parallel top/bottom surfaces.

The top/bottom surfaces of the carrier element also may be configured as trapezoids, which will permit material combinations (ambient media, carrier elements) for which the limiting angle of total reflection is greater than 45°.

DESCRIPTION OF THE DRAWINGS

Following is more detailed description of the invention as illustrated by the attached drawings, in which.

DETAILED DESCRIPTION OF THE PREFERRED EMBODIMENTS

Figure 1:
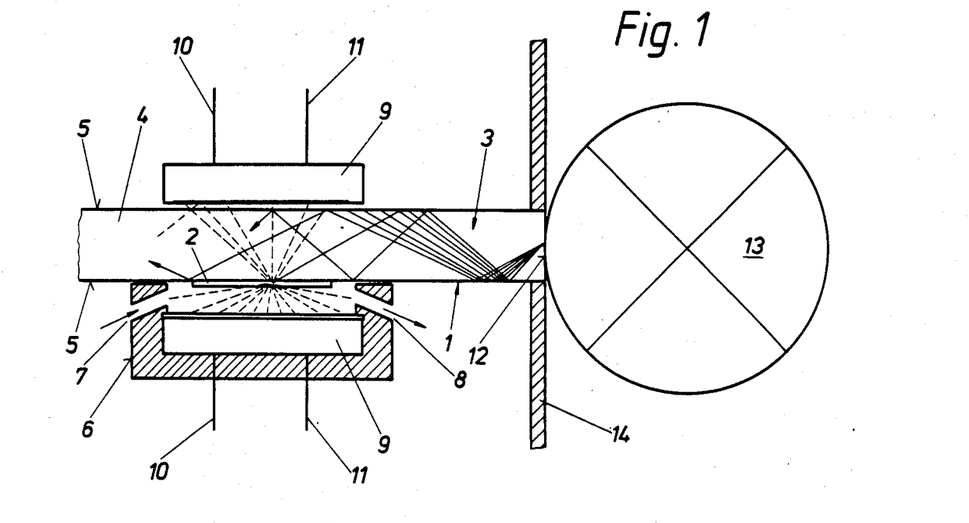
FIGS. 1 and 2 are sectional schematical views of different arrangement variants according to the invention.

The arrangement for optical measurement of the concentrations of substances contained in a sample, which is presented in FIG. 1, comprises a sensor element 1 with a carrier element 3 part of whose surface is coated with a layer of an indicator substance. On the side of this carrier element 3 covered with the indicator layer 2—the carrier element being configured as a plate 4 with parallel top and bottom surfaces 5—is provided a sample chamber 6 through which the sample to be measured may flow via an inlet 7 and an outlet 8.

Facing the indicator layer 2 a detector 9 is located inside the sample chamber 6, which is configured as a photodetector and delivers electrical signals corresponding to the radiation detected, to an evaluation unit (not shown here) via leads 10, 11. On the other side of plate 4, opposite the indicator layer 2, a further detector 9 is located on the parallel surface 5, which is basically of the same design as the one inside the sample chamber 6.

On a lateral boundary surface 12 of the plate 4, or the carrier element 3, which is essentially normal to the indicator layer 2, is located a light source 13 which sends excitation light via the face 12 into the interior of plate 4 which is transparent for the radiation used. In the area of the lateral boundary face 12 a screen 14 is provided in order to prevent direct illumination of the detectors 9 by the light source 13.

The carrier element 3, or rather the plane-parallel plate 4, has a refractive index for the radiation from the light source 13 which is greater than that of the ambient medium at the indicator-free surface of plate 4, such that—as shown—the excitation light from the light source 13 is propagated inside plate 4 by means of total reflection. Only in the area of the indicator layer 2 in which the refractive index is higher than that of the ambient medium so that total reflection no longer prevails and the light can leave through the boundary surface of plate 4, will it be possible for the excitation light to emerge from plate 4 and to enter the indicator layer 2. On account of the properties of the indicator material used which will interact, according to the respective physical and chemical laws, with the substance to be determined in the sample contained in sample chamber 6, luminescence is excited in the indicator layer 2 by the excitation light (indicated by full lines in FIG. 1); the light emitted in this way is indicated by broken lines in FIG. 1. Since the spectrum and/or intensity of the emission light will depend on the quantity to be measured, the signal from the detectors 9 may be used for determining this quantity or a change thereof.

Since due to the total reflection of the excitation light in the carrier element 3 no excitation light, with the exception of straylight components, will arrive at the detectors 9, and since, on the other hand, due to the specific geometry shown, the geometrical conditions for total reflection are not met at the parallel surfaces 5 for the light emitted by the indicator layer 2, no filters are required in front of the detectors 9 for spectral discrimination of excilation light and emission light. And, since the detectors 9 may therefore be placed in close vicinity of the indicator layer 2, this will allow a high yield of emission light without having to increase the intensity of the excitation light, thus improving measuring accuracy.

Figure 2:
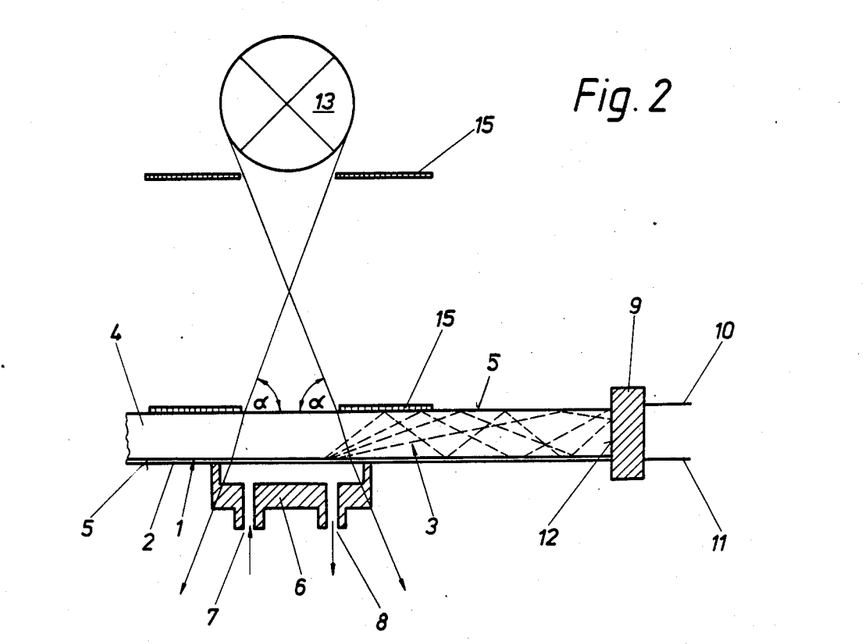

In the variant shown in FIG. 2 the light source 13 is placed in a position normal to the indicator layer 2 which in this instance covers the entire surface of the parallel face 5. By means of an aperture 15 the angle of incidence $\alpha$ of the excitation light is kept small, which will reduce partial reflection of the excitation light. Although the excitation light will be able to travel through the plane-parallel plate 4 as far as the indicator layer 2, it cannot reach the detector 9 positioned at the lateral boundary surface 12. The sample chamber again is marked 6, the inlet 7 and the outlet 8.

The light emitted by the indicator layer 2 in the area of the sample chamber 6, upon excitation by the light source 13 again, is indicated by broken lines; once a given distance has been reached from the sample chamber 6 in the direction towards the detector 9, the conditions for total reflection inside the carrier element 3 are again met. Therefore the arrangement of FIG. 2 again ensures that only emission light will reach the detector 9, without the additional use of filters.

Figure 3:
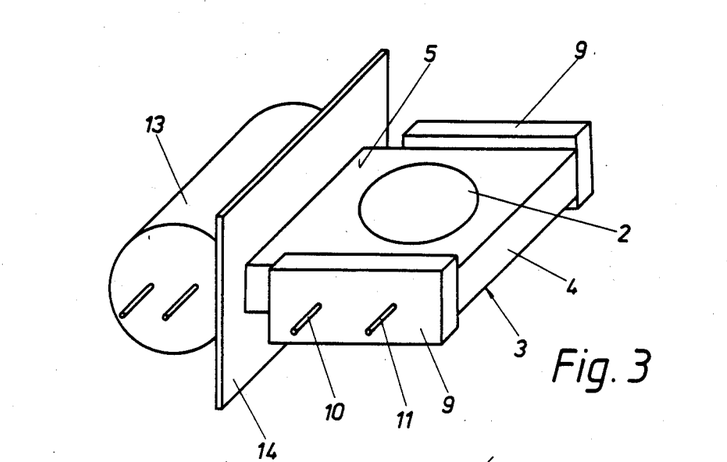
FIG. 3 is an oblique view of another variant.
Figure 3A:
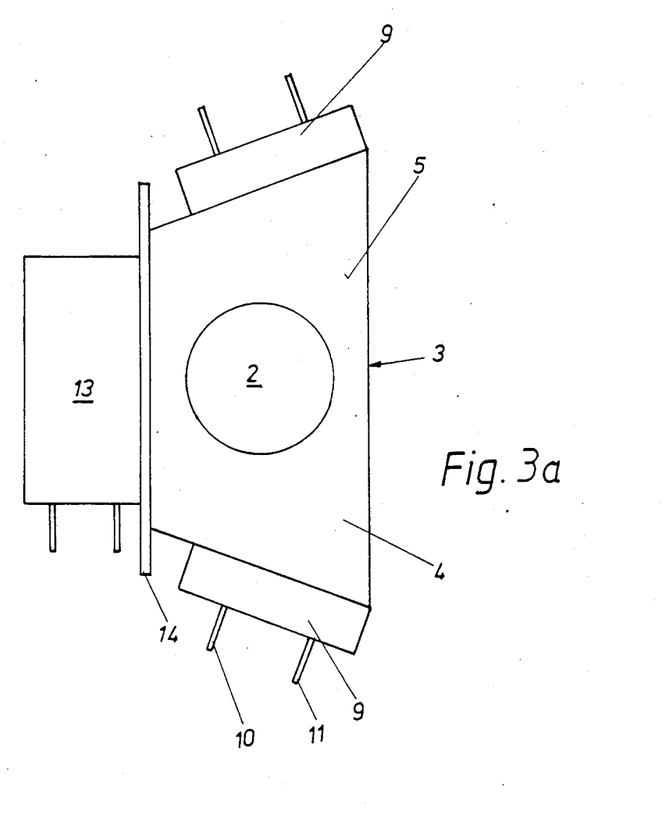
FIG. 3a shows a top plan view of another variant.

The variant presented in FIG. 3 basically is a combination of the arrangements of FIGS. 1 and 2. As in FIG. 1, the light source 13 is positioned at a lateral boundary surface of the carrier element 3, or rather of the plane-parallel plate 4 acting as a carrier element, and is separated by a screen 14. On two lateral boundary faces which are normal to the face with the light source, detector 9 are positioned; the indicator layer 2 is applied on a surface 5 which is normal to both lateral boundary surfaces, i.e., the one towards the detectors 9 and the one towards the light source 13; the sample chamber is not shown in this drawing. FIG. 3a shows a top plan view of another variant similar to that shown in FIG. 3 but wherein the lateral boundary surfaces of the plate are non-parallel and provide trapezoidal configurations to the top and bottom surfaces of the carrier element.

The specific geometry shown will guarantee that for the excitation light entering the carrier element 3—in view of the detectors 9 which are in a position normal to the entry face—the conditions for total reflection are satisfied at the faces of light emersion towards the detectors. In this manner the arrangements of FIGS. 3 and 3a ensures that light can be propagated from the excitation light source 13 to the indicator layer 2, and from the indicator layer 2 to the detectors 9, utilizing total reflection in the carrier element 3, and that, with the exception of straylight components, the detectors 9 will register emission light only. The use of excitation light filters for the straylight components may be of advantage in such an arrangement, very thin filters being sufficient.

Figure 4:
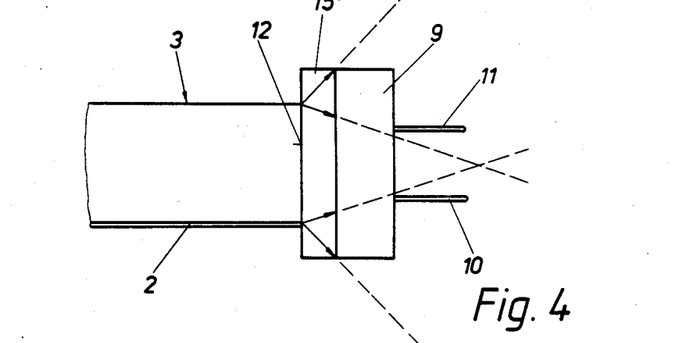
FIG. 4 is a schematical view of a detail from another variant.

FIG. 4 presents a coupling layer 15' between the lateral boundary face 12 of the carrier element 3 and the detector 9, which may consist of a polymer material, for example, that is directly applied on the detector 9. The retractive index of this coupling layer 15' is greater than that of the ambient medium of the carrier material, preferably exceeding or equalling that of the carrier element itself. In this way light transmission towards the detector 9 may be improved by the collimated effect of the coupling layer 15'.

Figure 5:
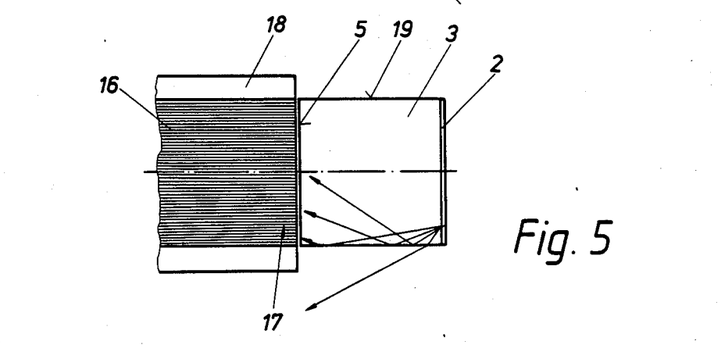
FIG. 5 shows a detail of yet another variant.

The detail shown in FIG. 5 is taken from an arrangement utilizing the frequently used technique of measuring luminescence by reflectance ("remission"). For this purpose a two-armed bundle of optical fibers 16 is provided, with a multitude of individual fibers utilizing total reflection, one arm of these fibers being in connection with a light source, and the other one being in connection with a detector, in a manner not shown here. The end 17 of the bundle of optical fibers 16 provided with a sleeve 18 is adjacent to a carrier element 3 for the indicator layer 2, which may have the shape of a cylinder or prism. By means of the side surface(s) 19 which is/are normal to the cover surface 5, excitation light is collimated onto the indicator layer 2, and emission light from the indicator layer is collimated towards the end 17 of the bundle of optical fibers 16. The same effect could be achieved by mirror-coating the side surface 19—utilization of total reflection inside the carrier element 3 will simplify manufacture, however.

Figure 6:
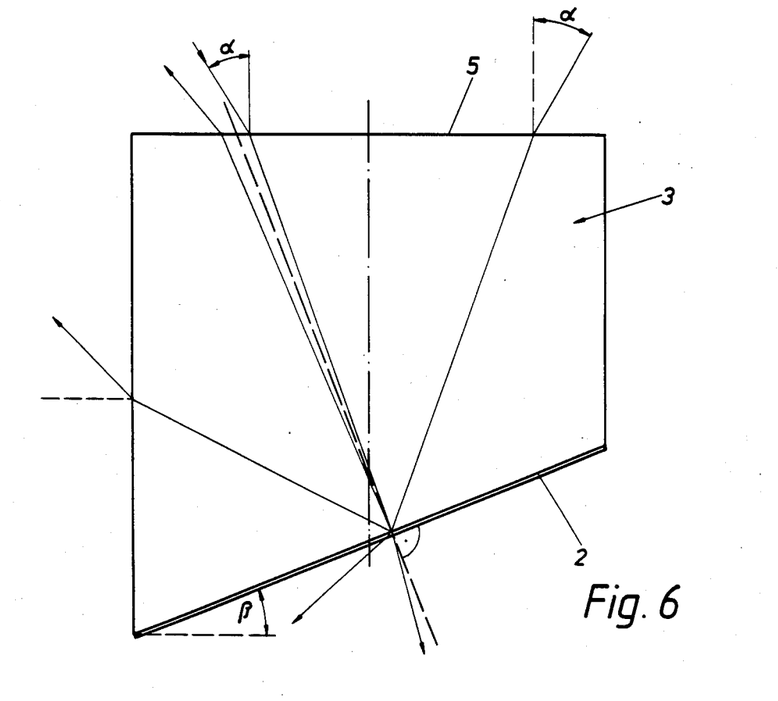
FIG. 6 presents the conditions of light reflection in a carrier element of a further variant according to the invention.

FIG. 6 shows a carrier element 3 for use in an arrangement as in FIG. 5, the bottom surface of the carrier element carrying the indicator layer 2 being inclined at an angle $\beta$ towards the top surface 5, in order to prevent partial reflection of the excitation light back into the optical fiber bundle not shown here. On the assumption that the maximum possible angle of emergence (in view of total reflection in the optical fiber) of light from the bundle of optical fibers into the ambient medium, equals $\alpha$, the angle $\beta$ must satisfy the following relations;

$$\sin\beta > \frac{\sin\frac{\alpha}{2}}{n_1};$$

$n_1$: refractive index of the carrier element 3

The above is based on the assumption that the ambient medium (e.g., air) at the side and top surfaces has the same refractive index.

Thus the inclination of the bottom surface carrying the indicator layer 2 will ensure that the excitation light which is partially reflected at this surface, cannot be transmitted back to the detector via the optical fiber bundle.

Figure 7:
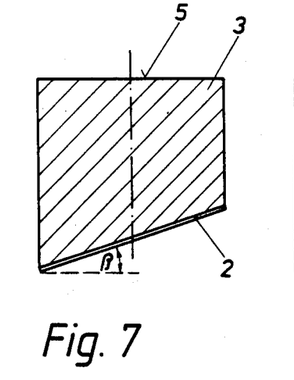
FIGS. 7 to 9 present different configurations of carrier elements for arrangements according to the invention.
Figure 8:
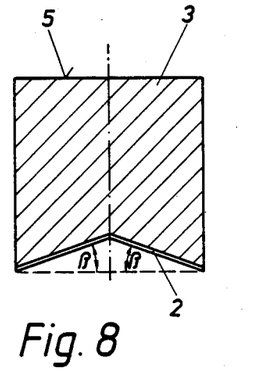
Figure 9:
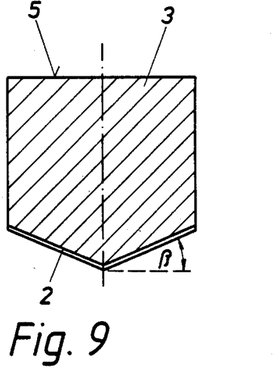

FIGS. 7 to 9 show various possibilities of producing the required inclination of the surface carrying the indicator layer 2 for a carrier element 3 configured as a cylinder or prism.

If the bundle of optical fibers is desired to be directly contiguous with the top surface of the carrier element (i.e., without a gap of air) or with an index-matched coupling layer in between, the differential refractive index in the above relation for $\beta$ might have to be taken into account separately.

We claim:

1. An arrangement for fluorescence-optical measurement of concentrations of substances contained in a sample, said arrangement being used in a surrounding ambient medium, comprising a light source for excitation radiation, a sensor element fluorescing upon excitation in accordance with substance concentration to be determined, and a detector for emission radiation, said sensor element comprising a carrier element which comprises at least two parallel surfaces and which is transparent for said excitation radiation and said emission radiation, said sensor element having a refractive index $n_1$ that is higher than the refractive index $n_3$ of a prevailing ambient medium, at least part of one of said surfaces of said carrier element being covered with a layer of an indicator substance of a given refractive index $n_2$, whose side facing away from said carrier element is in contact with said sample during the process of measurement, said excitation radiation having angles of incidence $\alpha_1$, measured from the normal on the boundary surface between said carrier element and said ambient medium, which are bigger than $\alpha_{G1,3} = \arc \sin n_3/n_1$, so that said excitation radiation is propagated in said carrier element by total reflection and wherein said excitation radiation has angles $\alpha_1$ smaller than $\alpha_{G1,2} = \arc \sin n_2/n_1$ in that area of said carrier element which is in contact with said sample via the indicator layer.

2. An arrangement according to claim 1, wherein said emission radiation reaching said detector has angles $\alpha_1$ bigger than $\alpha_{G1,3} = \arc \sin n_3/n_1$, so that said emission radiation is propagated in said carrier element by total reflection too.

3. An arrangement according to claim 2, wherein the boundary surfaces for entrance of excitation light and detection of emission light and said indicator layer are placed at positions normal to one another.

4. An arrangement for fluorescence-optical measurement of concentrations of substances contained in a sample, said arrangement being used in a surrounding ambient medium, comprising a light source for excitation radiation, a sensor element fluorescing upon excitation in accordance with substance concentration to be determined, and a detector for emission radiation, said sensor element comprising a carrier element which comprises at least two parallel surfaces and which is transparent for said excitation and said emission radiation, said sensor element having a refractive index $n_1$ that is higher than the refractive index $n_3$ of a prevailing ambient medium, at least part of one of said surfaces of said carrier element being covered with a layer of an indicator substance of a given refractive index $n_2$, whose side facing away from said carrier element is in contact with said sample during the process of measurement, said excitation radiation having angles of incidence $\alpha_1$, measured from the normal on the boundary surface between said carrier element and said indicator substance, which are smaller than $\alpha_{G1,2} = \arc \sin n_2/n_1$ in that area of said carrier element which is in contact with said sample via the indicator layer and wherein said emission radiation reaching said detector has angles $\alpha_1$ bigger than $\alpha_{G1,3} = \arc \sin n_3/n_1$, so that said emission radiation is propagated in said carrier element by total reflection.

5. An arrangement according to claim 4, with said carrier element being configured as a plate with parallel top and bottom surfaces and said indicator layer being applied on one of these surfaces, wherein said light source used for excitation is placed in a position essentially normal to said layer, and wherein said detector is positioned at least at one lateral boundary surface of said carrier element, which is essentially normal to said indicator layer.

6. An arrangement according to claim 5, wherein one top/bottom surface of said carrier element is completely covered by said indicator layer, and wherein the refractive index $n_2$ of said indicator layer is greater than the refractive index $n_3$ of said ambient medium.

7. An arrangement according to claim 6, wherein an aperture is provided between said light source and said carrier element, which will limit the angle of incidence of said excitation light.

8. An arrangement according to claim 5, wherein an aperture is provided between said light source and said carrier element, which will limit the angle of incidence of said excitation light.

9. An arrangement according to any of claims 6 to 7 wherein a coupling layer is provided between the lateral boundary surface of said carrier element facing the detector and the detector itself, which coupling layer has a refractive index $n_4$ greater than the refractive index $n_3$ of the ambient medium.

10. An arrangement according to claim 5, wherein a coupling layer is provided between the lateral boundary surface of said carrier element facing the detector and the detector itself, which coupling layer has a refractive index $n_4$ greater than the refractive index $n_3$ of the ambient medium.

11. An arrangement according to claim 10, wherein the refractive index $n_4$ of said coupling layer is greater than, or equal to, the refractive index $n_1$ of said carrier element.

12. An arrangement according to claim 10 or 11, wherein said coupling layer consists of a polymer material which is applied directly onto said detector.

13. An arrangement according to claim 5, wherein said top/bottom surfaces of said carrier element are configured as trapezoids.

* * * * *